(12) United States Patent
Brokopp et al.

(10) Patent No.: US 9,034,333 B2
(45) Date of Patent: May 19, 2015

(54) METHOD FOR TARGET AND DRUG VALIDATION IN INFLAMMATORY AND/OR CARDIOVASCULAR DISEASES

(75) Inventors: Chad Brokopp, Zurich (CH); Simon Hoerstrup, Zurich (CH)

(73) Assignee: University of Zurich, Zurich (CH)

( * ) Notice: Subject to any disclaimer, the term of this patent is extended or adjusted under 35 U.S.C. 154(b) by 0 days.

(21) Appl. No.: 13/819,416

(22) PCT Filed: Aug. 29, 2011

(86) PCT No.: PCT/EP2011/064839
§ 371 (c)(1),
(2), (4) Date: Feb. 27, 2013

(87) PCT Pub. No.: WO2012/025636
PCT Pub. Date: Mar. 1, 2012

(65) Prior Publication Data
US 2013/0164305 A1    Jun. 27, 2013

Related U.S. Application Data

(60) Provisional application No. 61/377,663, filed on Aug. 27, 2010, provisional application No. 61/431,515, filed on Jan. 11, 2011.

(30) Foreign Application Priority Data

Aug. 27, 2010  (EP) .................................... 10008937
Jan. 11, 2011  (EP) .................................... 11000146

(51) Int. Cl.
*G01N 33/50* (2006.01)
*A61K 38/00* (2006.01)

(52) U.S. Cl.
CPC ........ *G01N 33/5047* (2013.01); *G01N 33/5008* (2013.01); *A61K 38/00* (2013.01); *G01N 2333/70596* (2013.01)

(58) Field of Classification Search
None
See application file for complete search history.

(56) References Cited

FOREIGN PATENT DOCUMENTS

| EP | 1 862 805 | 12/2007 |
|---|---|---|
| WO | 2006/010517 | 2/2006 |
| WO | 2007/000292 | 1/2007 |
| WO | 2012/025633 | 3/2012 |

OTHER PUBLICATIONS

Ma (Modern Drug Discovery 2004, 7(6)).*
Vasan (Circulation. May 16, 2006;113(19):2335-62).*
Schlueter et al (Circulation. Jul. 21, 2009;120(3):255-63).*
Pericleous et al. British Journal of Cancer (2005) 93, 1257-1266).*
International Preliminary Report on Patentability from International Application No. PCT/EP2011/064839 dated Mar. 5, 2013, 9 Pages.
Wyss, Christopher A. et al. Cellular actors, Toll-like receptors, and local cytokine profile in acute coronary syndromes. European Heart Journal, Jun. 2010, vol. 31, No. 12, pp. 1457-1469.

* cited by examiner

*Primary Examiner* — Brian J Gangle
*Assistant Examiner* — Andrea McCollum
(74) *Attorney, Agent, or Firm* — MH2 Technology Law Group, LLP

(57) ABSTRACT

A novel method for validating the utility of a drug in the treatment of inflammatory and cardiovascular diseases is described.

10 Claims, 6 Drawing Sheets

METHOD FOR TARGET AND DRUG VALIDATION IN INFLAMMATORY AND/OR CARDIOVASCULAR DISEASES

CROSS-REFERENCE TO TED APPLICATIONS

This application is a U.S. National Stage application of PCT/EP2011/064839 filed 29 Aug. 2011, which claims priority to European patent application 10008937.4 filed 27 Aug. 2010, European patent application 11000146.8 filed 11 Jan. 2011, U.S. Provisional Patent Application 61/377,663 filed 27 Aug. 2010, and U.S. Provisional Patent Application 61/431,515 filed 11 Jan. 2011, the entire disclosures of which are hereby incorporated herein by reference in their entireties.

FIELD OF INVENTION

The present invention relates to methods, agents and kits for identifying and validating the efficacy of agents as therapeutic or diagnostic means in an inflammatory and/or cardiovascular disease.

BACKGROUND OF THE INVENTION

Chronic inflammatory diseases, such as coronary artery disease starts with the formation of atherosclerotic plaques in the coronary arteries. Abrupt occlusion of these atherosclerotic arteries due mainly to thrombosis leads to coronary heart diseases: unstable angina, acute myocardial infarction and sudden death. Coronary artery disease is a disease of several risk factors, among which are hyperlipidemia, hypertension, diabetes mellitus and tobacco smoking. The origin or cause of all stages of atherosclerotic cardiovascular diseases has been implicated by inflammation and is considered to be a major part of the pathophysiological basis of atherogenesis. Atherosclerosis is a degenerative inflammatory process that affects artery walls. Due to the lack of appropriate diagnostic markers, the first clinically presentation of more than half of the patients with coronary artery diseases is either myocardial infarction or death. Thrombotic diseases including myocardial infarction and stroke are currently the leading cause of death in the western world.

Rupture of the fibrous cap in so-called "vulnerable atherosclerotic plaques" is a critical trigger of myocardial infarction and stroke. Thereby vulnerable atherosclerotic plaques become thrombogenic by either rupturing open, or expressing pro-thrombotic agents which promote blood coagulation and occlude the coronary blood flow. Atherothrombosis is a term which describes the blood coagulation derived from atherosclerotic plaques to form so-called occluding "coronary thrombi". One of the key events involved in promoting plaque instability is degradation of the fibrous cap, which exposes the underlying thrombogenic plaque core to the bloodstream, thereby causing thrombosis and subsequent vessel occlusion. Thrombosis is the formation of a blood clot inside a blood vessel, obstructing the flow of blood through the circulatory system. When a blood vessel is injured, the body uses platelets and fibrin to form a blood clot to prevent blood loss.

Alternatively, even when a blood vessel is not injured, blood clots may form in the body if the proper conditions present themselves. When a thrombus occupies a significant surface area of the lumen of an artery, blood flow to the tissue supplied may be reduced to cause symptoms due to decreased oxygen (hypoxia) and accumulation of metabolic products like lactic acid. More than 90% obstruction can result in anoxia, the complete deprivation of oxygen, and infarction, a mode of cell death.

Coronary thrombus formation is orchestrated by myriad proteases whose enzymatic activities promote thrombosis via blood clotting. An understanding of the specific proteins which are expressed on each cell population may allow for identification of novel biomarkers and therapeutic targets against myocardial infarction. In addition, as myocardial infarctions often reoccur, a complete protein/cell description of individuals' thrombi may motivate personalized preventative treatment against reoccurring events. Unfortunately, the level of specific cell population as well as the proteins expressed by specific cell populations and their respective expression levels in coronary thrombi remain unknown.

It was not until 1980 that DeWood et al. (N Engl J Med 303 (1980), 897-901) provided definitive angiographic evidence that intracoronary thrombi have a causal role in the pathogenesis of acute coronary occlusion in acute myocardial infarction. Since then, coronary thrombi have proven practically difficult to retrieve from the infracted heart of living patients for diagnostics or pre-clinical research. However, recent advances in thrombus-retrieving catheter technology now allow well-equipped catheter labs to retrieve coronary thrombus material for analysis.

Nevertheless, though research in the process of the onset and development of chronic inflammatory disease have developed, means and methods of therapeutic intervention as well as a reliable diagnosis of conditions related to inflammatory and/or cardiovascular diseases still often suffer from severe side effects, low efficacy and unreliable prediction of disease state to name a few short-comings encountered in the art. This is probably because though a magnitude of possible novel therapeutic and diagnostic targets as well as methods of determining the same have been suggested, a reliable ex-vivo assay for selecting putative drugs and lead compounds for the development of a therapeutic and diagnostic agent for inflammatory and cardiovascular diseases has not been established yet.

Thus, there is a need for novel candidate therapeutic and diagnostic molecules capable of neutralizing and detecting pro-thrombotic targets, and which are specific to targeted cell populations for optimal safety and efficacy. In addition, candidate therapeutic or diagnostic molecules should specifically target cell populations involved in thrombus formation and not quiescent peripheral blood, as undesired side-effects may occur.

The solution to said technical problem is achieved by providing the embodiments as characterized in the claims and described further below.

SUMMARY OF THE INVENTION

The present invention relates to a method for determination or validation the utility of an agent, in particular antibodies or derivatives thereof for therapeutic or diagnostic means. More specifically, the present invention relates to the use of fluorescence activated flow cytometry for determining or validating the therapeutic or diagnostic utility of an agent for an inflammatory and/or cardiovascular disease, preferably wherein the cardiovascular disease or condition is a coronary atherothrombosis.

The present invention is based on a novel and surprising finding that the therapeutic and diagnostic ability of an agent for an inflammatory and cardiovascular disease can be reliably determined in human thrombus material compared to circulating blood or peripheral thrombus material of a patient by use of the flow cytometry technique. This technology is called "FACS-mediated thrombo-analysis" or "FMTA". In particular, the FMTA technology could be shown to be suitable for determining and validating candidate therapeutic and diagnostic agents illustrated by anti-FAP antibody. Therefore, the present invention provides a method for determining and validating the therapeutic or diagnostic utility of an agent for an inflammatory and/or cardiovascular disease comprising subjecting a putative agent to a sample of a thrombus obtained from a patient who had experienced an acute cardiovascular condition and determining the binding of the agent to at least one specific cell population and/or protein which is specific for the disease, wherein an altered level of binding of the agent to the cell population or protein compared to the level of binding in a control sample is indicative for the utility of the agent as a therapeutic or diagnostic means, characterized in that the binding is determined by fluorescence activated flow cytometry.

By this means, in one embodiment of the present invention an increased level of binding of the agent indicates its utility as a drug. Preferably, the agent comprises an antibody or a derivative thereof. In a preferred embodiment of the present invention, the agent is a human antibody.

In accordance with the present invention it could be surprisingly shown that specific binding of a candidate drug exemplified by an anti-FAP antibody to an altered cell number can be observed at least in one cell population selected from a group consisting of CD14 dim-hi monocytes, granulocytes, eosinophils, neutrophils, cytotoxic T-cells, double negative T-cells, helper T-cells and/or CD28-helper T-cells. In a further preferred embodiment of the present invention an altered protein level is observed at least in monocytes, eosinophils, neutrophils and/or granulocytes. Hence, in a preferred embodiment of the present invention, the level of the cell population and/or protein is altered in the thrombus sample compared to a control sample. In a preferred embodiment of the present invention, the level of the cell population relates to the number and/or status of the cells of said cell population. Typically, the expression of the protein is associated with said at least one specific cell population.

The sample in which specific binding is analyzed in accordance with the method of the present invention can be a thrombus material, wherein the thrombus can be derived from different origins of a subject. Preferably, the thrombus is a coronary thrombus. In a further embodiment of the present invention the control sample is selected from peripheral blood or a peripheral arterial thrombus.

In addition, in accordance with the present invention, as a control the sample is analyzed for the level of Fibroblast Activation Protein (FAP), preferably wherein the level of FAP is altered in at least one cell population.

In another embodiment, the present invention relates to an agent identified in accordance with the method mentioned above for use in the treatment or diagnosis of an inflammatory and/or cardiovascular disease, preferably wherein the agent has been determined to bind to at least one of the following cell population selected from the group consisting of CD14 dim-hi monocytes, granulocytes, eosinophils, neutrophils, cytotoxic T-cells, helper T cells, double negative T-cells and/or CD28 negative helper T-cells. Preferably, the agent is an anti-FAP antibody or derivative thereof.

In a further embodiment, the present invention also concerns a kit for use in the method of the present invention comprising at least one candidate antibody recognizing a putative agent; and optionally suitable means for detection.

Further embodiments of the present invention will be apparent from the description that follows.

DEFINITIONS AND GENERAL TECHNIQUES

Figure 1:
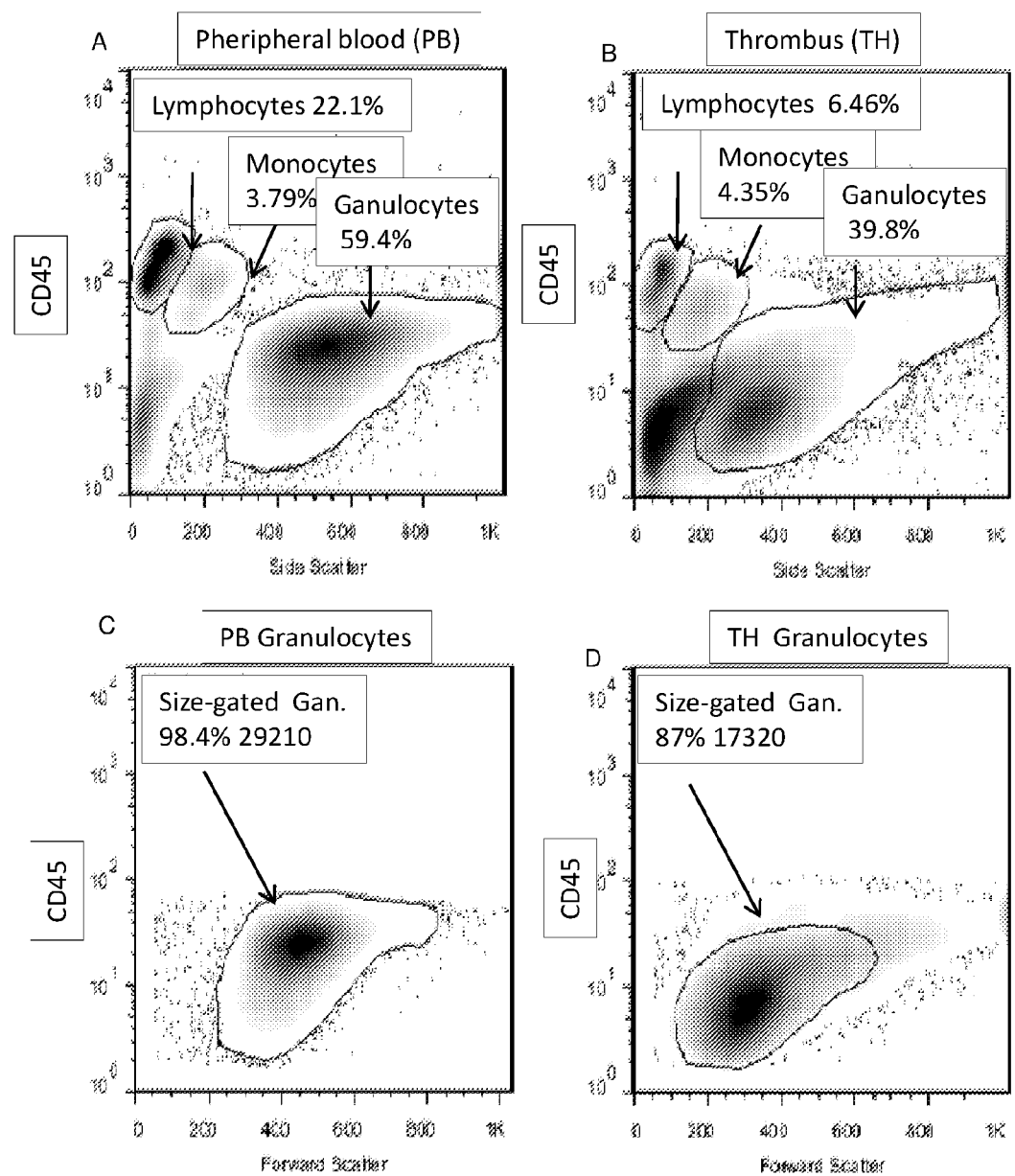
FIG. 1: Peripheral blood and thrombus leukocyte cell sets are defined by CD45 and granularity, followed by size-based gating. Representative lymphocyte, monocyte, and granulocyte cell populations are identified by CD45 and size scatter for peripheral blood (A) and thrombus samples (B). Granulocyte cell populations are further defined based on size and CD45 expression for both peripheral blood (C) and thrombus (D) specimens.

Unless otherwise stated, a term as uses herein is given the definition as provided in the Oxford dictionary of biochemistry and molecular biology, Oxford University Press, 1997, revised 2000 and reprinted 2003, ISBN 0 19 850673 2.

For further elaboration of general techniques useful in the practice of this invention, the practitioner can refer to standard textbooks and reviews in cell biology and tissue culture; see also the references cited in the examples. General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Non-viral Vectors for Gene Therapy (Wagner et al. eds., Academic Press 1999); Viral Vectors (Kaplitt & Loewy eds., Academic Press 1995); Immunology Methods Manual (Lefkovits ed., Academic Press 1997); and Cell and Tissue Culture: Laboratory Procedures in Biotechnology (Doyle & Griffiths, John Wiley & Sons 1998). Reagents, cloning vectors and kits for genetic manipulation referred to in this disclosure are available from commercial vendors such as BioRad, Stratagene, Invitrogen, Sigma-Aldrich, and ClonTech.

An "agent" as used in the context of the present invention relates primarily to antibodies, and derivatives thereof, but may also refer to other non-antibody molecules that bind to an epitope and/or neoepitope including but not limited to hormones, receptors, ligands, major histocompatibility complex (MHC) molecules, chaperones such as heat shock proteins (HSPs) as well as cell-cell adhesion molecules such as members of the cadherin, intergrin, C-type lectin and immunoglobulin (Ig) superfamilies. Thus, for the sake of clarity only and without restricting the scope of the present invention most of the following embodiments are discussed with respect to antibodies and antibody-like molecules which represent the preferred binding molecules for the development of therapeutic and diagnostic agents.

The term "antibody" furthermore refers to an immunoglobulin molecule that specifically binds to, or is immunologically reactive with, a particular antigen, and includes monoclonal, genetically engineered (e.g., rIgG) and otherwise modified forms of antibodies, including but not limited to chimeric antibodies, humanized antibodies, heteroconjugate antibodies (including, e.g., bispecific antibodies) and multimeric forms of antigen binding fragments, including, e.g., diabodies, triabodies and tetrabodies. In addition, unless otherwise indicated, the term "monoclonal antibody" (mAb) is meant to include both intact molecules, as well as, antibody fragments (such as, for example, Fab and F(ab')$_2$ fragments) which are capable of specifically binding to a protein. Fab and F(ab')$_2$ fragments lack the Fc fragment of intact antibody, clear more rapidly from the circulation of the animal or plant, and may have less non-specific tissue.

The term "antibody derivative or fragment" refers to a portion of a full-length antibody, generally the target binding or variable region. Examples of antibody fragments include Fab, Fab', F(ab')2 and Fv fragments. An "Fv" fragment is the minimum antibody fragment which contains a complete target recognition and binding site. This region consists of a dimer of one heavy and one light chain variable domain in a tight, non-covalent association (VH-VL dimer). It is in this configuration that the three CDRs of each variable domain interact to define a target binding site on the surface of the VH-VL dimer. Collectively, the six CDRs confer target binding specificity to the antibody. However, even a single variable domain (or half of an Fv comprising only three CDRs specific for a target) has the ability to recognize and bind target, although at a lower affinity than the entire binding site. "Single-chain Fv" or "scFv" antibody fragments comprise the VH and VL domains of an antibody, wherein these domains are present in a single polypeptide chain. Generally, the Fv polypeptide further comprises a polypeptide linker between the VH and VL domains which enables the scFv to form the desired structure for target binding.

Unless stated otherwise, the terms "disorder" and "disease" are used interchangeably herein.

In addition, the term "target" in accordance with the present invention denotes an epitope to a gene which is up- or down-regulated in a diseased cell and/or cell population of a subject having the disease relative to a counterpart normal cell. A target is indicative for which protein is sufficiently specific to the diseased cell and/or cell population that it can be used, optionally with other proteins, to identify or detect the disease. Generally, a target is a protein or a cell population that is characteristic of the disease. In addition, the term "neoepitope" is used interchangeably with the term "target" in accordance with the present invention and denotes an epitope which is unique for a disease pattern and contained in or formed by a disorder-associated protein which is a pathological variant from an otherwise non-pathological protein and/or deviating from the physiology of the healthy state. Said pathophysiological variants can be formed by means of pathologically altered transcription, pathologically altered translation, post-translational modification, pathologically altered proteolytic processing, pathologically altered complex formation with physiological or pathophysiological interaction partners or cellular structures in the sense of an altered co-localization, or pathologically altered structural conformation—like for example aggregation or oligomerization—whose three- or four-dimensional structure differs from the structure of the physiologically active molecule. In addition, a pathophysiological variant can also be characterized in that it is not located in its usual physiological environment or subcellular compartment. Whether a given structure, for example cell or tissue, or protein displays a neoepitope can be verified by reversing the method described below for isolating and characterizing a disorder-associated protein specific binding molecule in that a binding molecule, for example antibody identified by said method is used to screen a sample for binding to the antibody, thereby determining the presence of a neoepitope.

The term "marker", "biomarker" or "therapeutic target" as used herein refers to a molecule to be used as a target for analyzing a patient's test sample. In one embodiment examples of such molecular targets are proteins or peptides. Proteins or polypeptides used as a marker in the present invention are contemplated to include naturally occurring variants of said proteins as wells as fragments of said protein or said variant, in particular, immunologically detectable fragments. One of skill in the art would recognize that proteins which are released by cells or present in the extracellular matrix may be damaged, e.g., during inflammation, and could become degraded or cleaved into such fragments.

Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but may differ in their isoelectric point (PI) or molecular weight (MW), or both, e.g., as a result of alternative mRNA or pre-mRNA processing. The amino acid sequence of a variant is to 95% or more identical with the corresponding marker sequence. In addition, or in the alternative a marker polypeptide or a variant thereof may carry a post-translational modification as glycosylation, acylation, and/or phosphorylation.

By "specifically binds," or "specifically recognizes," used interchangeably herein, it is generally meant that a target or agent, e.g., an antibody binds to an epitope via its antigen binding domain, and that the binding entails some complementarities between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

As used herein, the terms "treat" or "treatment" refer to both therapeutic treatment and prophylactic or preventative measures, wherein the object is to prevent or slow down (lessen) an undesired physiological change or disorder, such as the development or spread of an inflammatory and/or cardiovascular disorder. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented.

An expression profile in one cell is "similar" to an expression profile in another cell when the level of expression of the proteins in the two profiles are sufficiently similar that the similarity is indicative of a common characteristic, e.g., being one and the same type of cell. Accordingly, the expression profiles of a first cell and a second cell are similar when at least 75% of the proteins that are expressed in the first cell are expressed in the second cell at a level that is within a factor of two relative to the first cell.

"Inhibitor" is any substance which retards or prevents a chemical or physiological reaction or response.

The terms "induce", "inhibit", "increase", "decrease" "lower" or the like, e.g., which denote quantitative differences between two states, refer to at least statistically significant differences between the two states. As used herein, "inhibiting the expression or activity" of an target refers to a reduction or blockade of the expression or activity, and does not necessarily indicate a total elimination of the expression or activity of a cell or a disease-associated protein. Such terms are applied herein to, for example, levels of expression, and levels of activity.

"Standard expression" is a quantitative or qualitative measurement for comparison. It is based on a statistical appropriate number of normal samples and is created to use a basis of comparison when performing diagnostic assays, running clinical trials or falling patient treatment profiles.

"Patient" as used herein might be defined to include human, domestic (e.g., cats, dogs etc.), agriculture (e.g., cows, horses, sheep etc.) or test species (e.g., mouse, rat, rabbit etc.).

The term "sample" as used herein refers to a biological sample obtained for the purpose of evaluation in ex vivo or in vitro. The patient and control sample may be discarded afterwards or stored under appropriate conditions until future use. Thereby, the stored sample may be used for further analysis or comparison means. The patient sample is solely used for the in vitro diagnostic method of the invention and the material of the patient sample is not transferred back into the patient's body. In the methods of the present invention, the sample or patient sample may comprise any body fluid or a tissue.

"Inflammatory disease" originates out of an inflammatory process. Inflammation is part of the non-specific immune response that occurs in reaction to any type of bodily injury. Inflammation has very specific characteristics, whether acute or chronic, and the innate immune system plays a pivotal role, as it mediates the first response. Infiltration of innate immune system cells, specifically neutrophils and macrophages, characterizes the acute inflammation, while infiltration of T lymphocytes and plasma cells are features of chronic inflammation. Monocytes/macrophages play a central role in both, contributing to the final consequence of chronic inflammation which is represented by the loss of tissue function due to fibrosis. In some disorders, the inflammatory process—which under normal conditions is self-limiting—becomes continuous and chronic inflammatory diseases might develop subsequently. Inflammatory disease is herein preferably understood as a chronic inflammatory disease such as inflammatory bowel disease, coronary artery disease, forms of arthritis, including rheumatoid arthritis, ankylosing spondylitis and osteoarthritis; tendinitis or tenosynovitis; inflammatory myopathies; inflammatory neuropathies; multiple sclerosis; epilepsy; inflammatory site edema; post-event ischemia and reperfusion symptomlogy resulting from acute central nervous system trauma, including stroke and spinal cord trauma; post-event consequences of kidney ischemia and reperfusion; and post-event consequences of reperfusion subsequent to myocardial infarction. In this context, the term "inflammatory disease" also includes conditions which are associated with inflammatory conditions such as referred to above, for example atherosclerosis and atherosclerotic plaque, and which otherwise may be regarded as cardiovascular diseases.

"In accordance with the present invention, the term inflammatory disease" is used herein to relate to chronic inflammatory diseases and in particular to cardiovascular diseases and inflammation. For further reading see Stitzinger "Lipids, inflammation and atherosclerosis at the digital repository of Leiden University (2007)."

The term "cardiovascular diseases" or "disorder" includes heart disorders, as well as disorders of the blood vessels of the circulation system caused by, e.g., abnormally high concentrations of lipids in the blood vessels.

As used herein, the term "atherosclerosis" is intended to have its clinical meaning. This term refers to a cardiovascular condition occurring as a result of lesion (e.g., plaque or streak) formation in the arterial walls. The formation of plaques or streaks results in a reduction in the size of the inner lining of the arteries. These plaques consist of foam cells filled with modified low-density lipoproteins, oxidized-LDL, smooth muscle cells, fibrous tissue, clumps of blood platelets, cholesterol, and sometimes calcium deposits. They tend to form in regions of disturbed blood flow and are found most often in people with high concentrations of cholesterol in the bloodstream. The number and thickness of plaques increase with age, causing loss of the smooth lining of the blood vessels and encouraging the formation of thrombi (blood clots).

As used herein an "atherosclerotic plaque" consists of accumulated intracellular and extracellular lipids, smooth muscle cells, connective tissue, and glycosaminoglycans. The earliest detectable lesion of atherosclerosis is the fatty-streak lesion comprising a lipid-laden foam cells, which are macrophages that have migrated as monocytes from the circulation into the subendothelial layer of the intima, which may later develop into the fibrous plaque, consisting of intimal smooth muscle cells surrounded by cognitive tissue and intracellular and extracellular lipids. As plaques develop, calcium may be deposited. Acute coronary events manifest when atherosclerotic plaque ruptures and blood comes into contact with the plaque's lipid content.

"Vulnerable atherosclerotic plaque" means when stable plaques become prone to rupture, which may lead to an acute event, such as thrombus formation and myocardial infarction. A characteristic of vulnerable plaque prone to rupture is a lipid core covered by a thin fibrous cap and inflammatory cells. Plaques with a thin fibrous cap, less than 65-μm thick, have been associated with acute coronary events. Such plaques may lose their stability and become unable to withstand circumferential stress, with subsequent rupture. The amount of lipid and composition of the lipid pool also promote plaque instability. Inflammation is a third factor affecting plaque vulnerability. Macrophages infiltrate the vessel wall and release proteases capable of degrading the intracellular matrix. Thinning of the fibrous cap is therefore central to atherosclerotic plaque rupture.

The "thrombus" is an aggregation of blood factors, primarily platelets and fibrin with entrapment of cellular elements, frequently causing vascular obstruction at the point of its formation. The lesion and the syndrome produced by the thrombus depends on its location, e.g., coronary artery.

As used herein, the term "coronary atherothrombosis" refers to systemic inflammatory disease states associated with complex inflammatory responses to multifaceted vascular pathologies involving inflammatory activation of the endothelium, inflammatory leukocytes as a source of thrombogenic stimuli, smooth muscle cells as a source of procoagulants and amplifier of the inflammatory response during thrombosis, and platelets as mediators of inflammation and thrombosis. Arteries harden and narrow due to buildup of a material called "plaque" on their inner walls. As the plaque develops and increases in size, the insides of the arteries get narrower ("stenosis") and less blood can flow through them. Stenosis or plaque rupture may cause partial or complete occlusion of the affected vasculature. Tissues supplied by the vasculature are thus deprived of their source of oxygenation (ischemia) and cell death (necrosis) can occur.

"One specific cell population" is a group of cells with characteristic proportions, such as granularity, size, shape and cell surface markers.

"Thrombosis" is the formation of a blood clot inside a blood vessel, obstructing the flow of blood through the circulatory system. When a blood vessel is injured, the body uses platelets and fibrin to form a blood clot to prevent blood loss. Alternatively, even when a blood vessel is not injured, blood clots may form in the body if the proper conditions are presented. When a thrombus occupies a significant surface area of the lumen of an artery, blood flow to the tissue supplied may be reduced to cause symptoms due to decreased oxygen (hypoxia) and accumulation of metabolic products like lactic acid. More than 90% obstruction can result in anoxia, the complete deprivation of oxygen, and infarction, a mode of cell death. Thrombotic diseases include, but are not limited to: myocardial infarction, stroke, venous thrombosis, deep vein thrombosis, portal vein thrombosis, renal vein thrombosis, jugular vein thrombosis, Budd-Chiari syndrome, Paget-Schroetter disease, cerebral venous sinus thrombosis, coronary stent occlusion, pulmonary embolism, and coronary bypass graft occlusion.

"Myocardial infarction" is the leading cause of death in the western world, and occurs when so-called "vulnerable atherosclerotic plaques" become thrombogenic by either rupturing open, or expressing pro-thrombotic agents which promote coagulation and occlude the coronary blood flow. Atherothrombosis is a term which describes the blood coagulation derived from atherosclerotic plaques to form so-called occluding "thrombi".

DETAILED DESCRIPTION OF THE INVENTION

The present invention generally relates to means and methods for research, prevention and treatment of an inflammatory and/or cardiovascular diseases like atherothrombosis. In particular, the present invention relates to means and methods for determining or validating a therapeutic or diagnostic utility of an agent for an inflammatory and/or cardiovascular disease. A putative agent is subjected to a sample of a thrombus obtained from a patient who had experienced an acute cardiovascular condition and the binding of the agent to at least one specific cell population and/or protein which is specific for the disease is determined. Thereby, an altered level of binding of the agent to the cell population or protein compared to the level of binding in a control sample is indicative for the utility of the agent as a therapeutic or diagnostic means. The binding is determined by fluorescence activated flow cytometry.

The present invention is based on a novel and surprising ex vivo method describing for the first time a method which quantifies candidate antibody specificity to cell populations in thrombi compared to cell populations in peripheral blood cell associated protein expression and cell population numbers which are altered in human thrombus material compared to circulating blood or peripheral thrombus material. This method makes use of the technology which is called "FACS-mediated thrombo-analysis" or "FMTA". FMTA uses thrombus biopsies and peripheral blood harvested from one patient, followed by enzymatic treatment to generate comparable single cell suspension for analysis by flow cytometry. In one embodiment, the present invention relates to a method of determining and/or validating the utility of an agent useful as a drug for therapeutic and diagnostic means. Candidate therapeutic antibodies and/or agents aimed at neutralizing pro-thrombotic targets should be specific to targeted cell populations for optimal safety and efficacy. Moreover, candidate therapeutic antibodies and/or agents should specifically target cell populations involved in thrombus formation and not quiescent peripheral blood, since candidate antibody-based drugs which erroneously bind quiescent cell populations in peripheral blood may not be specific to thrombosis, and therefore carry potentially adverse side effects, and limited efficacy due to binding unintended targets. Furthermore, the absence of cross-reactivity with physiological precursors or derivatives leads to the consequence that, first, the concentrations are predictable as sink effects in healthy tissue structures are avoided and, second, that autoimmune responses in the sense of undesired side effects are substantially missing. The FMTA technology of the present invention provides a profile of candidate therapeutic antibody and/or agent binding to each cell population in thrombi compared to peripheral blood. As demonstrated in the Examples, the present invention provides for the first time a procedure to measure antibody and/or agent specificity to individual cell population of human peripheral blood compared to human thrombi. FMTA may be also be used to compare cell and cell-associated protein levels, and cell population numbers between thrombi and peripheral blood in order to determine the specific binding of a drug to selected cell-populations or proteins which are indicative for an inflammatory and/or cardiovascular disease. For example, and as demonstrated in Example 6, the monoclonal F19 anti-FAP (mF19) antibody has been determined to be a candidate antibody-based drug since it exhibits an altered binding specificity for the diseased thrombi sample i.e. to the respective epitope of the cell-associated protein compared to the control. In addition, neutrophil binding by mF19 is enhanced in coronary thrombi compared to peripheral blood. Furthermore, mF19 binding to peripheral blood eosinophils is enhanced in myocardial infarction patients compared to patients with peripheral thrombosis. Taken together, the data from this example shows that mF19 binds to coronary thrombus specific neutrophils, which supports the notion of its specificity towards thrombosis. Additionally, mF19 binding is also enhanced in peripheral blood eosinophils of patients with a myocardial infarction, compared to non-infarct patients; suggesting also a potential unintended effect on this population. Therefore, one object of the present invention is determining specific binding of candidate therapeutic antibodies in peripheral blood cell populations compared to thrombus cell populations; thereby providing evidence of antibody specificity and efficacy. A further object of the present invention is determining the underlying mechanisms of atherothombosis. Thereby the present invention provides also personalized treatments since individual thrombi of a patient can be used in order to test and verify a putative therapeutic agent to increase the rationale of a successful treatment in order to prevent re-occurring thrombotic events. Therefore, the present invention provides for the first time an agent identified by the above-mentioned method for use in the treatment or diagnosis of an inflammatory or cardiovascular disease. Thus, being useful for the treatment of patients being at the risk, suffering from a myocardial infarction, stroke or experienced a cardiovascular condition.

In particular, the present invention relates to a method for determining or validating the therapeutic or diagnostic utility of an agent for an inflammatory and/or cardiovascular disease comprising subjecting a putative agent to a sample of a thrombus obtained from a patient who had experienced an acute cardiovascular condition and determining the binding of the agent to at least one specific cell population and/or protein which is specific for the disease, wherein an altered level of binding of the agent to the cell population or protein compared to the level of binding in a control sample is indicative for the utility of the agent as a therapeutic or diagnostic means, characterized in that the binding is determined by fluorescence activated cytometry.

In a preferred embodiment, the present invention relates to an agent which is capable of selectively recognizing an epitope which may be or may not be a disease-associated protein including a neoepitope of a disease-associated protein, which therapeutic or diagnostic use can preferably can be determined or validated by the method of the present invention as described herein before and illustrated in the Examples. Advantageously, the pre-determined agent of the present invention exhibits an altered binding specificity to its epitope recognized in a thrombus sample compared to the control sample which is indicative for its adequacy as a drug or biomarker.

Hence, the present invention relates to drugs comprising such binding molecules, antagonists, antibodies and mimics thereof and to methods of determining or validating for pre-determined agents and/or binding molecules, which may or may not be antibodies, agents and/or drugs in the treatment of various disorders, in particular inflammatory and/or cardiovascular disorders.

The agent and/or drug is not limited to antibodies, therefore, in a further embodiment, the present invention relates to an antagonists of the pro-thrombotic target, for example, molecules which, when bound to the pro-thrombotic target, decrease the amount of the duration of the activity of the pro-thrombotic target. Inhibitors or antagonists are capable of inhibiting the activity of the pro-thrombotic target polypeptide, mRNA or DNA level or its expression refers to a change in the activity of the pro-thrombotic target, by decreasing the enzymatic activity or by affecting transcription or translation of the pro-thrombotic target, binding characteristics or any other biological, functional or immunological properties of the pro-thrombotic target. Antagonists may be peptides, proteins, nucleic acid, carbohydrates, antibodies, small organic compounds, peptide mimics, aptamers or PNAs (Milner, Nature Medicine 1 (1995), 879-880; Hupp, Cell 83 (1995), 237-245; Gibbs, Cell 79 (1994), 193-198; Gold, Ann. Rev. Biochem. 64 (1995), 736-797). In a preferred embodiment of the present invention, the agent comprises an antibody or derivative thereof. Preferably, the agent is an anti-FAP antibody or derivative thereof.

In another embodiment of the present invention, the agent can block or reduce expression of pro-thrombotic targets, e.g., by reducing transcription or translation of pro-thrombotic target mRNA, or reducing the stability of pro-thrombotic target mRNA or protein. In another embodiment, the agent is an inhibitor of the expression or translation of a pro-thrombotic target nucleic acid such as a double-stranded RNA (dsRNA) molecule, microRNA (miRNA), an antisense molecule, a ribozyme, a triple-helix molecule, or any combination thereof. In one preferred embodiment of the present invention the agent is capable of binding to pro-thrombotic target or its encoding nucleic acid molecule. Typically, the agent of the present invention is a small molecule, e.g., a chemical agent, a small organic molecule, e.g., a product or a combinatory of natural product library, a polypeptide, e.g., an antibody such as an pro-thrombotic target specific antibody, a peptide, a peptide fragment, e.g., a substrate fragment, a peptidometic or a modulator. The agent can also be antagonists of a pro-thrombotic target polypeptide and can be compounds that exert their effect on the pro-thrombotic target activity via the enzymatic activity, expression, post-translational modifications or by other means.

In another object of the present invention, antibodies or derivatives thereof may be used in a method for the diagnosis of a disorder in an individual by obtaining a thrombus sample from the tested individual and contacting the thrombi sample with an antibody or derivative thereof under conditions enabling the formation of antibody-antigen complexes. The level of such complexes is then determined by flow cytometry or methods known in the art, a level significantly higher than that formed in a control sample indicating the disease in the tested individual. In the same manner, the specific antigen bound by the antibodies or derivatives thereof may be used as also outlined below. In a preferred embodiment, an increased level of binding of the agent indicates its utility as a drug. In a preferred embodiment, the agent comprises an antibody or a derivative thereof.

Antibodies of the present invention may be used in non-conjugated form or may be conjugated to at least one of a variety of molecules, e.g., to improve the therapeutic properties of the molecule, to facilitate target detection or for imaging or therapy of the patient. Antibodies, or antigen-binding fragments, variants or derivatives thereof of the invention can be labeled or conjugated either before or after incubation with the target cells. Preferred means for detecting a level, i.e. a decrease or increase of complex formation between the antibody and its at least one interacting molecule or an increased or decreased binding capacity compared to a control by, for example, labels comprising fluorescent label, phosphorescent label, radioactive label, which are known to those skilled in the art. In a preferred embodiment of the present invention, the antibody is detectably labeled. Thereby the antibodies are directly or indirectly labeled. Suitable further fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Suitable optical dyes are described in the 1996 Molecular Probes Handbook by Richard P. Haugland, the disclosure content of which is herein incorporated by reference.

Figure 3:
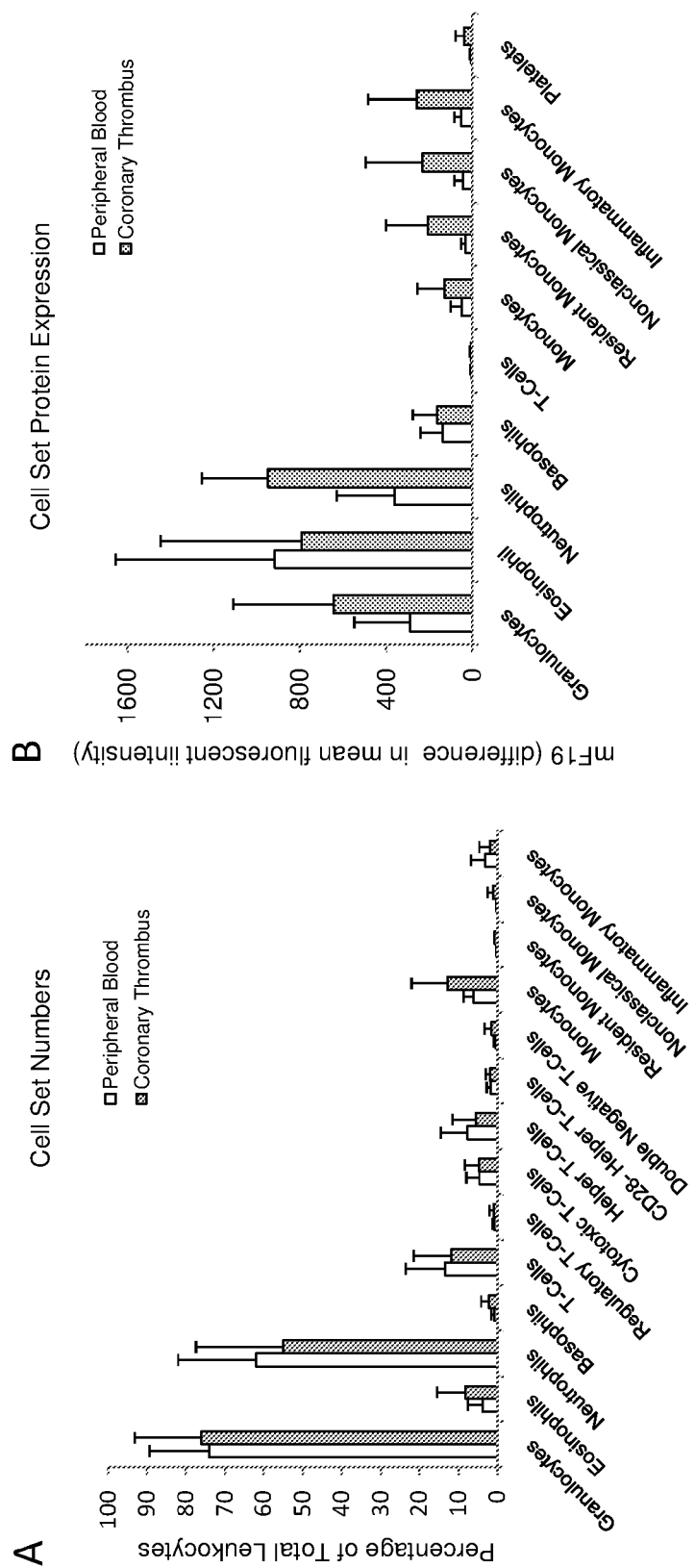
FIG. 3: Representative data from coronary FMTA analysis. (A) Cell set numbers as a percentage of total leukocytes and (B) cell-set specific protein expression (FAP; Fibroblast Activation Protein) is shown as a result of coronary FMTA.

In one embodiment of the present invention the method comprises contacting a sample with a monoclonal and/or polyclonal antibody or a derivative thereof as a candidate biomarker or drug which binds specifically to the altered protein or cell population of the thrombi sample thereby indicating its therapeutic or diagnostic ability. Any type of antibody or a derivative thereof known to be potential candidate for the treatment or diagnosis can be analyzed for specifically binding to an epitope of altered protein or cell population which has been revealed in accordance with the present invention and identified in the Examples and shown in FIGS. 3 to 5. The present invention also features that the respective gene product is determined by the candidate antibody which can be a polyclonal antibody, a monoclonal antibody, a human antibody, humanized antibody, a chimeric antibody, a recombinant antibody and a synthetic antibody. Suitable methods and guidance for the generation of human antibodies are described in detail in the international application WO 2008/081008 the disclosure content of which is herein incorporated by reference. Antibody as used herein includes intact immunoglobulin molecules, as well as fragments thereof, such as Fab, F(ab')$_2$, and Fv, which are capable of binding an epitope of a therapeutic or diagnostic agent. The production of chimeric antibodies is described, for example, in international application WO89/09622. Methods for the production of humanized antibodies are described in, e.g., European application EP-A1 0 239 400 and international application WO90/07861. A further source of antibodies to be utilized in accordance with the present invention are so-called xenogeneic antibodies. The general principle for the production of xenogeneic antibodies such as human-like antibodies in mice is described in, e.g., international applications WO91/10741, WO94/02602, WO96/34096 and WO 96/33735. As discussed above, the antibody of the invention may exist in a variety of forms besides complete antibodies; including, for example, Fv, Fab and F(ab)$_2$, as well as in single chains; see, e.g., international application WO88/09344. The perceived advantages of using small Fab and scFv engineered antibody formats which lack the effector function lies in minimizing the risk of triggering inflammatory side reactions. Furthermore, besides scFv and single-domain antibodies retain the binding specificity of full-length antibodies, they can be expressed as single genes and intracellularly in mammalian cells as intrabodies, with the potential for alteration of the folding, interactions, modifications, or subcellular localization of their targets; see for review, e.g., Miller and Messer, Molecular Therapy 12 (2005), 394-401. In a different approach Muller et al., Expert Opin. Biol. Ther. (2005), 237-241, describe a technology platform, so-called 'SuperAntibody Technology', which is said to enable antibodies to be shuttled into living cells without harming them. Such cell-penetrating antibodies open new diagnostic and therapeutic windows. The term 'TransMabs' has been coined for these antibodies. However, the present invention is not limited to antibodies. Therefore, in a preferred embodiment of the present invention the antibody or derivative thereof is selected from the group consisting of single Fc fragment (scFv), an F(ab') fragment, an F(ab) fragment and an F(ab')$_2$ fragment.

However, as described herein before, in particular with respect to therapeutic applications in the antibody of the present invention is a human antibody. Alternatively, the antibody is a human IgG isotype antibody, a chimeric human-murine or murinized antibody, the latter being particularly useful for diagnostic methods and studies in animals. In this context, the variant pathological protein recognized by the antibody is preferably associated with a cardiovascular disorder.

Thus, the present invention relates to specific binding molecules, particularly human antibodies as well as fragments, derivatives and variants thereof that recognize endogenous proteins, disease-associated epitopes, including neoepitopes, of proteins which derive from native endogenous proteins, and which are prevalent in the body of a patient in a variant form and/or out of their normal physiological context or endogenous proteins or fragments thereof which are enhanced expressed in cells.

The results presented in the Examples as well as in the corresponding Figures of the present invention indicate the following novel discoveries CD14 dim-hi monocytes, eosinophils, cytotoxic and double negative T-Cell subsets, CD28-Helper T-Cells numbers are increased in human coronary thrombi sample compared to matched peripheral blood samples. In addition, neutrophil numbers and Helper T-Cells are decreased in human coronary thrombi samples compared to matched peripheral blood samples. Furthermore, eosinophil numbers and cytotoxic T-Cell subsets are increased in human peripheral thrombi samples compared to peripheral blood. Also it has been discovered that inflammatory monocyte subsets are decreased in peripheral blood compared to a peripheral thrombi sample. In addition, the results of the present invention disclose that that a specific binding of a candidate drug antibody exemplified by an anti-FAP antibody could be shown to be altered in cell-associated protein expression in a thrombus sample of a patient who had experienced a myocardial infarction. Furthermore, the results presented in the Examples indicate that a specific binding of a candidate drug antibody exemplified by an anti-FAP antibody could be shown to be enhanced in granulocyte as well as monocyte in coronary thrombi compared to a peripheral thrombi sample.

Hence, the present invention also provides the FMTA technology which precisely quantifies cell-associated protein expression and cell populations numbers which are altered in human thrombus material compared to circulating blood or peripheral thrombus material in a subject suffering from a cardiovascular condition in order to reveal the ability of an antibody or fragment thereof as biomarker or drug. Thus, in a preferred embodiment of the present invention, the expression of the protein is associated with said at least one specific cell population.

The coronary thrombi samples can be analyzed with the help of the FMTA technology of the present invention in order to elucidate the specific cell-associated protein and/or cell population binding of an agent. Thereby, a human control sample is assessed in order to provide reference data for comparison and evaluation of the obtained results from the coronary thrombus sample. Control samples which could be analyzed according to the above-mentioned method include blood, serum, plasma, sputum bronchial lavage, tissue samples like thrombus, plaque or sputum, wherein preferred however, in accordance with the method of the present invention the control sample is selected from peripheral blood or a peripheral aterial thrombus.

The skilled artisan will appreciate now that FMTA technology is useful in the assessment of an inflammatory and/or cardiovascular disease. Determining or validating the utility of a therapeutic or diagnostic agent by measuring the binding specific to cell-associated protein levels and cell population numbers can also be achieved by various immunodiagnostic procedures or assays and may be used to reach a result comparable to the achievements of the present invention.

In a preferred embodiment of the present invention, analyzing the sample comprises an immunoassay. Suitable immunoassays can be applied in either a direct or indirect format, like, for example, particle immunoassays, radioimmunoassay (RIA), enzyme (EIA) immunoassay, fluorescent immunoassay (FIA) or chemiluminescent immunoassays. A variety of protocols for detecting and measuring the expression of cell and cell-associated protein levels, and cell population numbers, using either polyclonal or monoclonal antibodies or fragments thereof specific for intracellular polypeptides/antigens and/or cell-surface markers, is known in the art. An antibody which specifically binds to an epitope of a protein or cell of interest can be used therapeutically, as well as in immunoassays, such as Western blots, ELISA, ELISpot and immunoprecipititations. ELISA can be used, including direct or indirect, sandwich and cell-culture enzyme-linked immunoabsorbent assay (ELISA) ELISpot. The Enzyme-Linked ImmunoSpot (ELISpot) assay is a very sensitive immunoassay, depending on the substance analyzed, the ELISpot assay is between 20 and 200 times more sensitive than a conventional ELISA. General formats and protocols for the conduct of various formats of ELISA are disclosed in the art and are known to those of skill in the field of diagnostics. For example, reference may be made to Chapter 11 of Ausubel (Ed) Current Protocols in Molecular Biology, $5^{th}$ ed., John Wiley & Sons, Inc, NY, 2002. The Immunoassay Handbook. 3rd ed. Elsevier Science Publishing Company, Amsterdam, Boston, Oxford 2005.

Other screening methods include Magnetic activated cell sorting (MACS), as described in Gaines (1999) Biotechniques 26(4):683-688. In addition, cell fluorescence activated cytometry and/or cell sorting (FACS) or other immunochemical assays known in the art such as acoustic focusing cytometry which is reported to have increased sensitivity compared to non acoustic focusing cytometry. While in accordance with the present invention, i.e. for the immediate use of FMTA, this level of specificity is not absolutely required, acoustic focusing cytometry may be useful in future "high-sensitivity" applications, wherein a therapeutic or diagnostic targets are expressed on a low level in order to precisely quantify these proteins. See for further reading Curtis et al., IBM Technical Disclosure Bulletin 25(1), (1982), Yasuda et al., J Acoust Soc Am 102 (1997), 642-645, Jonsson et al., Perfusion 20 (2005), 39-43 and the U.S. Pat. No. 7,340,957 the disclosure content of which is herein incorporated by reference. General information and protocols are disclosed in Raem, Arnold M. Immunoassays. 1st ed., Munich; Heidelberg: Elsevier, Spektrum Akademischer Verlag., 2007; David Wild (Ed.): The Immunoassay Handbook. 3rd ed. Elsevier Science Publishing Company, Amsterdam, Boston, Oxford 2005. FACS analysis can comprise flow cytometry as well as fluorescence activated cell sorting, wherein the conventional flow cytometry allows the analysis of fixed and permeabilized cells which are after analysis discarded. Fluorescence activated cell sorting is used to sort individual cells on the basis of optical properties, including fluorescence. It is used to screen large populations of cells in a relatively short period of time; thereby the sorted cells can be further processed or analyzed by suitable means. Further reference to protocols means and methods can be obtained from the art Ormerod, M. G. (ed.) (2000) Flow Cytometry—A practical approach. 3rd ed. Oxford University Press, Oxford, UK ISBN 0199638241, Handbook of Flow Cytometry Methods by J. Paul Robinson ISBN 0471596345, et al. Current Protocols in Cytometry, Wiley-Liss Pub. In a preferred embodiment of the present invention, the assay comprises fluorescence activated cytometry (flow cytometry). In order to classify and count cells of interests as well as measure their cell-associated proteins at the same time conventional flow cytometry will be the best choice. Flow cytometry is a method of analyzing cell sub-populations, using automated equipment. It is widely used in medical labs and in biomedical and biochemical research, and it is discussed in various books and articles such as Flow Cytometry and Sorting, M. R. Melamed et al. (eds) Wiley and Liss, 1990 and in journals such as Cytometry and the American Journal of Clinical Pathology. As an example for classifying and counting cells of interest, these are fixed and incubated with fluorescent dyes. The immunofluorescence of cells is known by a person skilled in the art and is the most widespread application of flow cytometry. Given an appropriate antibody, any protein in the cell or on the cell-surface, which is present in a high enough concentration, can be measured. Several antigens can be measured simultaneously; routinely, a person skilled in the art measures between 3 and 5 antigens although machines have been built which can record up to 17 different colors; for further reading see for example Baumgarth and Roederer J. Immunol. Methods 243 (2000), 77-97, the disclosure content of which is herein incorporated by reference.

In addition, use of flow cytometry for measuring the size and morphological features of cells are not specifically limited. The low angle scattered light of an internal laser beam reflects the size of cells and the high angle scattered light reflects the morphological features of cells. As a measuring parameter which reflects the cell size, electric resistance can be used. Thereby, flow cytometry displays all sub-types of cells of a population as well as their cell-associated proteins of interests at the same time.

In a preferred embodiment of the present invention the therapeutic or diagnostic target to be identified or validated are determined with fluorescently labeled tags, and therefore, protein amounts and/or cell numbers are relative to the detected signal intensity. This signal intensity can be quantified as the mean fluorescent intensity (MFI). By subtracting the mean fluorescent intensity of the non-specific isotype control antibody (background) from the signal given by the protein-specific antibody, in this manner, a quantitative measure of protein amount can be calculated. As mentioned in the methods section in the Examples, infra, each cell population in every sample can be gated according to standardized levels (measured by positive control samples compared to isotype controls) and in consideration of references from the scientific literature. However, the person skilled in the art knows that slight manual adjustment of the gates are necessary to accommodate for inevitable patient specific differences and inter-sample variability. Representative gating in accordance with the present invention is demonstrated in the Examples, in particular in Example 1 and 2 and the corresponding Figures.

In a further embodiment of the present invention, more than one type of cell population can be analyzed, for example leukocytes, macrophages, endothelial cell or smooth muscle cell. Leukocytes include inflammatory CD14-positive/CD16-positive monocytes, resident CD14-positive/CD16-negative monocytes, granulocytes including basophiles, neutrophils and eosinophils, B-Cells, T-Cells including Helper-, Cyotoxic-, Memory-, Regulatory-, Natural Killer-, double negative (CD4–/CD8–)-, platelets, and gamma delta T-Cell subsets. Thus, one embodiment of the present invention, the level of the cell population relates to the number and/or status of the cells of said cell population, preferably wherein an altered cell number is observed in at least one cell population selected from the group consisting of CD14 dim-hi monocytes, granulocytes, eosinophils, neutrophils, cytotoxic T-cells, double negative T-cells, Helper T-cells and/or CD28-Helper T-cells; and/or wherein an altered protein level is observed at least in monocytes, eosinophils, neutrophils and/or granulocytes.

Advantageously, a candidate agent exhibit in at least one of the above-mentioned cell population an altered binding level, however an increased binding to more than one cell population is preferred. In a further preferred embodiment the cell population comprises leukocytes. In accordance with the method of the present invention, the candidate therapeutic agent is analyzed for an increased or decreased binding to leukocyte cell populations and/or respective cell distribution profile in a thrombus or blood sample. In a preferred embodiment of the present invention, the binding of the agent correlates to an altered level of the cell population and/or the protein.

In a preferred embodiment according to the present invention, the level of the cell population and/or the protein is altered. In this context it should be understood that "altered" in general means an increase or decrease of protein expression or the respective activity and/or an increase as well as a decrease of cell numbers compared to the corresponding protein expression or cell population numbers of the control sample. In addition, the term "level" is used in accordance with the present invention, as the respective expression or activity level of the putative therapeutic or diagnostic target.

The FMTA technology of the present invention provides a simple, fast and reliable method for analyzing the cell populations of interest by using standardized levels (measured by positive control samples compared to isotype controls) as mentioned in the Examples, and each cell population in every sample can be identified, i.e. gated in consideration of references from scientific literature. Without intending to be bound by theory, using flow cytometry analysis, single cell suspension of different types of cell populations can be analyzed, which are obtained from the patient, such as leukocytes including inflammatory CD14-positive/CD16-positive monocytes, and resident CD14-positive/CD16-negative monocytes, CD14 dim-hi monocytes, granulocytes including basophils, neutrophils and eosinophils, B-Cells, T-Cells including Helper-, Cyotoxic-, Memory-, Regulatory-, Natural Killer-, double negative (CD4–/CD8–)-, platelets, and gamma delta T-Cell subsets, thrombi-associated proteins or smooth muscle cells. In a preferred embodiment according to the present invention, an altered cell number is observed in at least one cell population selected from the group consisting of CD14 dim-hi monocytes, granulocytes, eosinophils, neutrophils, cytotoxic T-cells, double negative T-cells, Helper T-cells and/or CD28-Helper T-cells. Preferred, according to the present invention, an altered protein level is observed at least in monocytes, eosinophils, neutrophils and/or granulocytes.

Thus, in accordance with the present invention a candidate agent exhibit a different binding capacity to the following cell populations or protein-associated cell populations in a sample of a patient suffering from coronary atherothrombosis: CD14 dim-hi monocytes, eosinophils, cytotoxic T-cells, double negative T-cells, CD28-Helper T-cells, granulocyte associated FAP and neutrophil associated FAP.

In a preferred embodiment, the patient is a human suffering from, or is at a risk of an inflammatory and/or a cardiovascular disease or condition and developed a thrombus. In one embodiment of the present invention, the cardiovascular disease or condition is coronary atherothrombosis. As explained in detail above, coronary atherothrombosis is a systemic inflammatory disease and atherothrombosis is the underlying condition that results in serious disease and complications such as: coronary artery disease, angina pectoris, heart attack, sudden death, cerebrovascular disease, stroke, transient ischemic attack (mini stroke) peripheral arterial disease (PAD) which may affect the abdominal aorta (aortic dissection) and its major branches, such as the superior mesenteric artery which supplies the intestine, or the renal arteries that supply the kidneys, and the arteries of the legs and arms. Preferably, the coronary atherothrombosis is selected from a group consisting of myocardial infarction, stroke, venous thrombosis, deep vein thrombosis, portal vein thrombosis, renal vein thrombosis, jugular vein thrombosis, Budd-Chiari syndrome, Paget-Schroetter disease, cerebral venous sinus thrombosis, coronary stent occlusion, pulmonary embolism or coronary bypass graft occlusion.

A person skilled in the art knows that there is at least a transient total or subtotal coronary occlusion in all cases of acute myocardial infarction. Hence, the analyzed thrombi material in accordance with the method of the present invention is an occluding coronary thrombus obtained from a patient who had experienced an acute myocardial infarction or is an occluding coronary thrombus obtained from a patient who had experienced peripheral artery occlusion. Therefore, the method according to the present invention makes use of this knowledge by providing a method of determining or validating the therapeutic or diagnostic utility of an agent against those diseases, wherein an occluding coronary thrombus is analyzed. In a preferred embodiment, the thrombus is a coronary thrombus.

The method of the present invention allows also the direct comparison of thrombus material derived from different origin. Thus, in a further embodiment of the present invention, the thrombus is selected from the group consisting of traditional atherothrombotic coronary thrombus, coronary stent thrombus, coronary bypass thrombus, peripheral arterial thrombus, pulmonary emboli or venous thrombus.

Thanks to the present invention, for the first time, a procedure to fast and precise determining the efficiency of a putative diagnostic or therapeutic agent is provided by measuring its binding capacity to the cell population numbers and cell-specific protein expression in human thrombi. FMTA may be used to compare the antigen-complex formation of cell and cell-associated protein levels between thrombi and peripheral blood or peripheral arterial thrombi. In addition, thrombus material of different origin can be compared directly against each other, including, but not limited to: traditional atherothrombotic coronary thrombi, coronary stent thrombi, coronary bypass thrombi, peripheral arterial thrombi, pulmonary emboli, and venous thrombi.

For example, a human thrombus sample taken from a patient who had experienced an acute myocardial infarction can be compared to a control sample taken from the same patient and assayed for the specific binding of a therapeutic or diagnostic agent of the cell-associated protein levels between the thrombus and the control sample. Strong binding to cell-associated protein in the thrombus sample which exhibits an altered expression compared to the control sample indicates that this putative therapeutic or diagnostic target can be used as a drug or biomarker, i.e. for its therapeutic or diagnostic means. Proteins of interest against which the therapeutic agent or diagnostic biomarkers should exhibit an increased binding affinity include those which may be involved in thrombogenesis, or those which are altered.

In accordance with the above, the method of the present invention provides a procedure to measure and/or validate thereby a therapeutic or diagnostic utility of a candidate antibody or binding fragment thereof by using the FMTA technology. When a putative therapeutic or diagnostic agent is analyzed for the first time, known proteins should also be investigated as a control. For example, the mF19 antibody against the protein Fibroblast Activation Protein (FAP) can be used. As described in detail in the European patent application EP 10 008 937.4 as well as in the U.S. provisional application 61/377,663 "A novel diagnostic and therapeutic target in inflammatory and/or cardiovascular diseases" filed on Aug. 27, 2010, the disclosure content of which is herein incorporated by reference, FAP is a marker for the presence and onset of a cardiovascular diseases. As evident from the Examples and the corresponding Figures of the present invention, it could be surprisingly shown that the binding level of mF19 anti-FAP antibody is altered in at least one cell population of a thrombus sample of a patient suffering from a myocardial infarction. In particular, the present invention revealed that granulocyte and neutrophil associated mF19 anti-FAP binding efficiency is enhanced in coronary thrombi compared to peripheral blood. In addition, as also evident from Example 5, the mF19 anti-FAP antibody binding level is also enhanced in the cell populations of granulocytes, monocytes and neutrophils in coronary thrombi compared to peripheral thrombi. Thus, in a preferred embodiment of the present invention, the level of mF19 anti-FAP antibody binding is altered in at least one cell population.

Naturally, the present invention extends to the use of an above-identified putative target which has been determined or validated with the claimed method as a therapeutic or diagnostic agent. Thus, in a further embodiment, the present invention relates to an agent identified in the method described herein before for use in the treatment or diagnosis of an inflammatory and/or cardiovascular disease, preferably wherein the agent has been determined to bind to at least one of the following cell population selected from the group consisting of CD14 dim-hi monocytes, granulocytes, eosinophils, neutrophils, cytotoxic T-cells, double negative T-cells and/or CD28-Helper T-cells. In particular, as shown in the Examples of the present invention, the FMTA technology revealed that the anti-FAP antibody mF19 could be specifically detected in the above-mentioned cell-populations to be also associated with the FAP protein. Thus, the present invention provides for the first time a putative therapeutic or diagnostic agent which has been validated by the method of the present invention using the novel FMTA technology.

A person skilled in the art will appreciate that the candidate antibodies or derivatives thereof which have been determined or validated by the method of the present invention are suitable for use in the treatment or prevention of an inflammatory and/or cardiovascular disease. As such, these diagnostic or therapeutic antibodies or fragments thereof are useful in diagnosing patient specific thrombotic situation and motivates personalized preventative treatment against reoccurring myocardial infarctions. In pre-clinical research, this method may be employed to determine the underlying mechanisms of atherothrombosis.

In accordance with the present invention and deducted from the experimental considerations below, see Example 3, mF19 exhibit an altered binding affinity to leukocyte cell populations. Therefore, in a preferred embodiment of the present invention, the cell population is CD14 dim-hi monocytes, granulocytes, eosinophils, neutrophils, cytotoxic T-cells, double negative T-cells and/or CD28-Helper T-cells.

Naturally the present invention extents to the use of the antibody or derivative thereof as determined or validated by the method described herein for the treatment of a patient suffering from or being at the risk to experience an cardiovascular condition such as a myocardial infarction or stroke. Thereby the patient has been analyzed for the target of the drug with the above mentioned method. Thus, in a further aspect, the present invention relates to an agent identified in the method described herein above for use in the treatment or diagnosis of an inflammatory and/or cardiovascular disease. Furthermore, the agent as mentioned above, which is a human antibody.

In a preferred embodiment the present invention relates to a drug for use in the treatment of a subject suffering from an inflammatory or cardiovascular disease, wherein the patient has been analyzed for the target of the drug in accordance with the method of the present invention. In particular, the drugs of the present invention may be antibodies, or antigen-binding fragments, variants, or derivatives thereof and may be conjugated to therapeutic agents, prodrugs, peptides, proteins, enzymes, viruses, lipids, biological response modifiers, pharmaceutical agents, or PEG. Conjugates that are immunotoxins including conventional antibodies have been widely described in the art. The toxins may be coupled to the antibodies by conventional coupling techniques or immunotoxins containing protein toxin portions can be produced as fusion proteins. The antibodies as mentioned above can be used in a corresponding way to obtain such immunotoxins. Illustrative of such immunotoxins are those described by Byers, Seminars Cell. Biol. 2 (1991), 59-70 and by Fanger, Immunol. Today 12 (1991), 51-54.

In certain embodiments, the drug is an antibody polypeptide which comprises an amino acid sequence or one or more moieties not normally associated with an antibody. Exemplary modifications are for example, a single-chain fv antibody fragment of the validated agent may comprise a flexible linker sequence, or may be modified to add a functional moiety (e.g., PEG, a drug, a toxin, or a label such as a fluorescent, radioactive, enzyme, nuclear magnetic, heavy metal and the like). In addition, antibodies may be recombinantly fused or conjugated to molecules useful as labels in detection assays and effector molecules such as heterologous polypeptides, drugs, radionuclides, or toxins; see, e.g., international applications WO92/08495; WO91/14438; WO89/12624; U.S. Pat. No. 5,314,995; and European patent application EP 0 396 387.

The present invention also provides a pharmaceutical and diagnostic, respectively, pack or kit comprising one or more antibodies recognizing at least one type of a cell population of a thrombus which has been shown in accordance the present invention to be altered. In addition, the kit comprises an agent which has been identified as a putative therapeutic or diagnostic agent associated with puffers, solvents secondary labeled agents in order to detect the primary antibody. In addition or alternatively, the kit comprises reagents and/or instructions for use in appropriate diagnostic assays. The kit of the present invention is of course particularly suitable for the diagnosis, prevention and treatment of a disorder which is accompanied with the presence of a disorder-associated protein as defined above, especially myocardial infarction, and in particular applicable for the treatment of inflammatory and/or cardiovascular atherothrombosis. Preferred is a kit for the use in the method described herein comprising at least one candidate agent; and optionally suitable means for detection.

The kit of the present invention is preferably suitable for commercial manufacture and scale and can still further include appropriate standards, positive and negative controls. Said kit containing specific reagents such as those described herein before further comprising for example selectable markers, reference samples, antibodies, and maybe some monitoring or detection means. Antibodies which are able to recognize specifically surface markers of leukocytes subtypes in order to distinguish the respective subclasses of leukocytes are included in the kit. In a preferred embodiment, the kit as described above, comprising an anti-CD45, anti-CD14, anti-CD66b, anti-CD16, anti-CD125, anti-CD133, anti-CD4, anti-CD25, anti-CD8, anti-CD34 and/or anti-CD3 antibody; and optionally an anti-FAP antibody.

Thereby, the aforementioned molecules, i.e. antibodies of said kit are specific for the new identified therapeutic or diagnostic agent identified by the method of the present invention. Furthermore, the kit may comprise an anti-Fibroblast Activation Protein (FAP) antibody as (a) to identify a patient suffering from or being at a risk of an inflammatory and/or cardiovascular disease or as (b) a control in order to confirm that an analyzed patient sample is suffering from an inflammatory and/or cardiovascular disease and compare the putative identified biomarker antibody with FAP antibody binding capacity towards the FAP protein expression level to further characterize said putative agent.

Preferably, the kit further comprises means for detecting a level, i.e. a decrease or increase of complex formation between the antibody and its at least one interacting molecule or an increased or decreased binding capacity compared to a control by, for example, labels comprising fluorescent label, phosphorescent label, radioactive label, which are known to those skilled in the art. In a preferred embodiment of the present invention, the antibody is detectably labeled. Thereby the antibodies are directly or indirectly labeled. Suitable further fluorescent labels are described in detail above. In a further preferred embodiment according to the present invention, said label is a fluorescent tag.

The above disclosure generally describes the present invention. Several documents are cited throughout the text of this specification. The contents of all cited references (including literature references, issued patents, published patent applications as cited throughout this application and manufacturer's specifications, instructions, etc.) are hereby expressly incorporated by reference; however, there is no admission that any document cited is indeed prior art as to the present invention.

A more complete understanding can be obtained by reference to the following detailed description and experiments which is provided herein for purposes of illustration only and is not intended to limit the scope of the invention.

EXAMPLES

The examples which follow further illustrate the invention, but should not be construed to limit the scope of the invention in any way. Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd ed. (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al., Bioprocess Technol. 19 (1990), 251); Extracting information from cDNA arrays, Herzel et al., CHAOS 11, (2001), 98-107.

Materials and techniques for design and construction of labeled antibodies and other agents for use in cytometry are known in the art and described for example, in Bailey et al. (2002) Biotech. Bioeng. 80(6); 670-676; Carroll and Al-Rubeai (2004) Expt. Opin. Biol. Therapy 4:1821-1829; Yoshikawa et al. (2001) Biotech. Bioeng. 74:435-442; Meng et al. (2000) Gene 242:201-207; Borth et al. (2001) Biotechnol. Bioeng. 71 (4):266-273; Zeyda et al. (1999) Biotechnol. Prog. 15:953-957; Klucher et al. (1997) Nucleic Acids Res. 25(23):4853-4860; and Brezinsky et al. (2003) J. Imumunol. Methods 277:141-155.

Experimental Procedures
Sample Harvesting
Coronary Thrombi

Human occluding coronary thrombi from patients who had experienced an acute myocardial infarction were retrieved using a catheter and placed directly into PBS at 4° C. One vial of peripheral blood from the same patient was taken at the same timepoint as a control.

Peripheral Artery Thrombi

Human thrombi from patients who had experienced a peripheral artery occlusion are retrieved using a catheter and placed directly into PBS at 4° C. One vial of peripheral blood from the same patient are taken at the same timepoint as a control.

Thrombolysis

Peripheral blood (1 mL) and the thrombus material are placed into 1 mL of ACCUTASE® (cell detachment solution) with 50 µL ACTILYSE® (tissue plasminogen activator), and shaken gently at 37° C. for 1 hr. Cell aggregates are further dissociated by forcing them through a cell strainer (40 µm pore size) using the soft rubber from a syringe. Both samples are then spun at 400 G for 5 min and the supernatant removed.

Cell pellets are then resuspended in FACS buffer (PBS with 1% FCS and 5 mM EDTA) with 1 μg/mL for Fc receptor blocking agent and incubated for 30 min at 4° C. Cells are then labeled with fluorescently tagged antibodies presented in Table 1 below, purchased from Becton Dickinson (Basel, Switzerland), Abcam (Cambridge, United Kingdom), and

TABLE 1

Antibody profiles for cell population gating.

| Cell | Characterization |
|---|---|
| T (thymus) Cells | CD3+ CD45+ |
| Regulatory T Cells | CD4+ CD25+ CD127 low |
| Cytotoxic T Cells | CD3+ CD8+ CD4− |
| Helper T Cells | CD3+ CD8− CD4+ |
| CD28-negative helper T Cells | CD4+ CD3+ CD28− |
| Double negative (CD4− CD8−) T Cells | CD3+ CD8− CD4− |
| Granulocytes | CD66b+ CD45+ |
| Eosinophils | CD66b+ CD125+ SSC (side scatter) high CD45+ |
| Neutrophils | CD66b+ CD125− SSC high CD45+ |
| Basophils | CD66b+ CD125− SSC low CD45+ |
| Monocytes | CD14 low and high CD45+ |
| Proinflammatory Monocytes | CD14+ CD16− CD45+ |
| Nonclassical Monocytes | CD14low CD16+ CD45+ |
| Thrombocytes | CD41a+ SSC low |
| Resident Monocytes | CD14+ CD16+ CD45+ |

Santa Cruz (Santa Cruz, CA).

Cell Fixation and Red Blood Cell Lyses

Cells are washed 2× in FACS buffer, fixed for 30 min in 1% PFA in PBS with 5 mM EDTA and then permeabilized with 1% TRITON™ X-100 in FACS buffer. Permeabilization also lyse the red blood cells which are then removed with the supernatant after centrifugation at 400 G for 5 min. Cells are then stained with a labeled antibody against the protein target of interest (in this example Fibroblast Activation Protein) or candidate therapeutic antibody of interest (mF19), washed twice, and then stored in FACS buffer with 1% PFA until analysis (up to 48 hours later).

Cell Population Gating

Each cell population in every sample can be gated according to standardized levels (measured by positive control samples compared to isotype controls) and references from the scientific literature. However slight manual adjustment of the gates might be necessary to accommodate for inevitable patient specific differences and intra-sample variability. Representative gating is shown in Example 1 and 2 Thromboanalysis Representative Gating).

Antibody Specificity Assay

To determine antibody binding to cell populations, each population are labeled with fluorescently tagged antibodies. Therefore, antibody binding are relative to the detected signal intensity. This signal intensity can be quantified as the mean fluorescent intensity (MFI). By subtracting the mean fluorescent intensity of the non-specific isotype control antibody (background) from the signal given by the protein-specific antibody, a quantitative measure of antibody binding, namely, "difference mean fluorescent intensity" is calculated as:

$$MFI-background=\text{difference mean fluorescent intensity}$$

Statistical Analyses

FMTA results are compared using a one-way ANOVA and associations calculated by Pearson's correlation coefficient. All statistical analyses are performed using MatLab (Version, R2007b). Data are presented as mean±SD. Significance is accepted at the level of $p<0.05$.

Example 1

Peripheral Blood and Thrombus Leukocyte Cell Sets are Defined by CD45 and Granularity, Followed by Size-Based Gating Human occluding coronary thrombi are retrieved from patients who had experienced an acute myocardial infarction as indicated, supra. One vial of peripheral blood from the same patient is taken at the same time point as a control. In order to quantify relative cell population from the thrombi (a solid form of clotted blood) the sample is gently lysed into individual cells in preparation of a flow analysis. This one hour procedure is performed by enzymatic digestion described in the methods above. Peripheral blood from the same patient is processed in an identical manner as the thrombus, and then the cells are stained with spectrally distinct fluorescently labeled antibodies. No secondary antibodies are used in order to avoid high background. Antibodies for cell typing are purchased from Becton Dickinson, which recognize proteins of interest on each cell populations as indicated in Table 1. Peripheral blood and thrombus leukocyte cell sets are defined by CD45 and granularity, followed by size-based gating. Representative lymphocyte, monocyte, and granulocyte cell populations are identified by CD45 and size scatter for peripheral blood (FIG. 1 A) and thrombus samples (FIG. 1 B). Granulocyte cell populations are further defined based on size and CD45 expression for both peripheral blood (FIG. 1 C) and thrombus (FIG. 1 D) specimens.

Example 2

Figure 2:
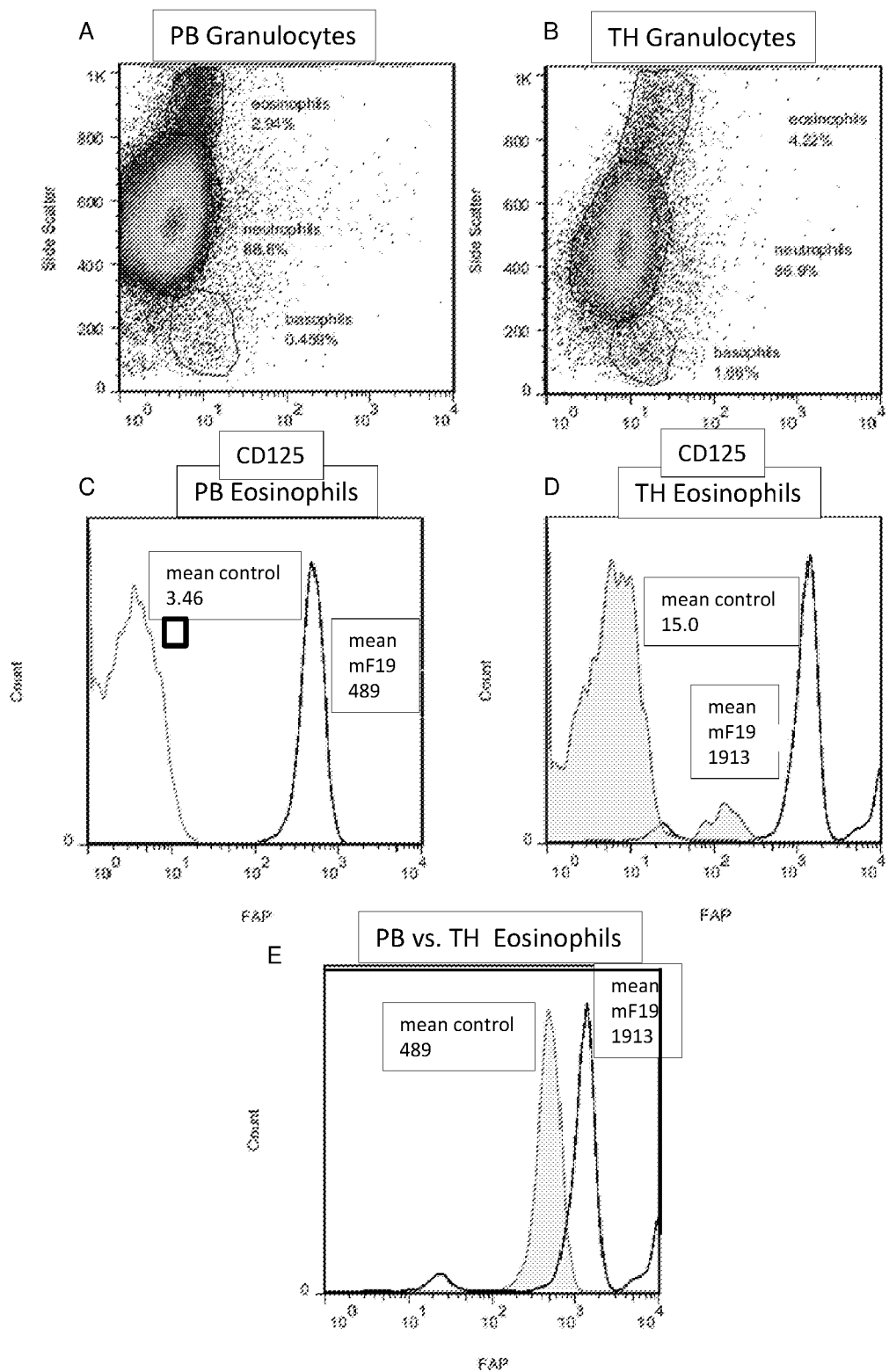
FIG. 2: Representative granulocyte subset gating for cell population-associated protein expression. Granulocytes pre-gated by CD66b/side scatter and forward scatter, are further gated into granulocyte subsets by CD125 and side scatter in peripheral blood (A) and thrombus specimens (B). From these gates, eosinophil-specific FAP expression is quantified as the mean fluorescent intensity from the histogram generated by an FAP-specific antibody (mF19) and a matching isotype control antibody for both peripheral blood (C) and thrombi (D). The increase of eosinophil-specific FAP expression is shown by the change of mean fluorescent intensity of the mF19 histogram for peripheral blood and thrombi (E).

Eosinophil-Associated FAP Expression is Enhanced in Peripheral Blood vs. Coronary Thrombi The samples are treated as indicated above, labeled with the respective antibodies as depicted in Table 1 and subjected to flow analysis. The anti-FAP antibody (mF19) has been prelabelled with a Cy5 antibody labeling kit from Sigma Aldrich. Granulocytes are first gated by CD66b expression and side scatter in peripheral blood and thrombi specimens. From this gate, granulocyte-specific FAP expression is quantified as the mean fluorescent intensity from the histogram generated by an FAP-specific antibody (mF19 provided by ATCC-LGC (Molsheim Cedex, France) and a matching isotype control antibody (Abcam) for both peripheral blood and thrombi. Furthermore, FAP expression in eosinophils pregated by side scatter and CD125, is quantified as the mean fluorescent intensity from the histogram generated by an FAP-specific antibody (mF19) and a matching isotype control antibody for both peripheral blood (FIG. 2 A) and thrombi (FIG. 2 B) in dot blot analysis. The increase of eosinophil-specific FAP expression is shown by the change of mean fluorescent intensity of the mF19 histogram for peripheral blood (FIG. 2 C) and thrombi (FIG. 2 D) in cell counts per fluorescence intensity. FIG. 2E shows the comparison of mF19 fluorescent intensity in peripheral blood vs. coronary thrombi, to illustrate enhanced FAP mF19 binding in the thrombus-derived cell population.

Example 3

Representative Data Using FMTA to Analyze Human Coronary Thrombus Cell Population Numbers and Cell Population-Specific Protein Expression in Comparison to Peripheral Blood Human occluding coronary thrombi are retrieved from patients who had experienced an acute myocardial infarction.

One vial of peripheral blood from the same patient is taken at the same time point as a control. In order to quantify relative cell population and protein levels from the thrombi (a solid form of clotted blood) the samples are gently lysed into individual cells in preparation of a flow cytometry analysis. This one hour procedure is performed by enzymatic digestion described in the methods above. In general, the samples are processed in a similar way as described in Example 2 and described in the methods, see supra. Peripheral blood from the same patient is processed in an identical manner as the thrombus, and then the cells are gated as described in Example 1 and 2 and cell populations are identified by staining the samples with the respective antibodies as indicated in Table 1. A: Cell populations as indicated in FIG. 3A are compared (as a percentage of the total leukocyte population) between peripheral blood and coronary thrombi specimens in the same patients (A; paired two-tailed student's T-test (FIG. 3A). Granulocyte, T-cell, and monocyte cell populations are compared (as a percentage of the total leukocyte population) between peripheral blood and coronary thrombi specimens in the same patients (A; paired two-tailed student's T-test). The absolute number of leukocytes is determined as the sum of total granulocytes, lymphocytes, and monocytes. Cytotoxic and double negative T-Cells as well as CD28-Helper T-Cells subsets are enhanced, whereas Helper T-Cells are decreased and Regulatory T-Cells numbers remain unchanged. T-Cell subsets are shown as a percentage of total leukocytes in peripheral blood versus coronary thrombi in the same patients. Total T-Cells are calculated by the absolute number of T-Cells gated by CD3 expression, granularity, and size. B: In addition, FIG. 3B depicts cell-set specific protein expression of Fibroblast Activation Protein as analyzed by fluorescence intensity and as described in Example 2, see supra, in leukocyte subtypes as indicated (B; paired two tailed student's T-test). This procedure allowed differential analysis of FAP expression on major coronary thrombi cell populations (FIG. 3B). As a result, the FAP is elevated specifically in granulocytes, neutrophils, monocytes, basinophils but not T-Cells in an occluding coronary thrombus.

Example 4

Figure 4:
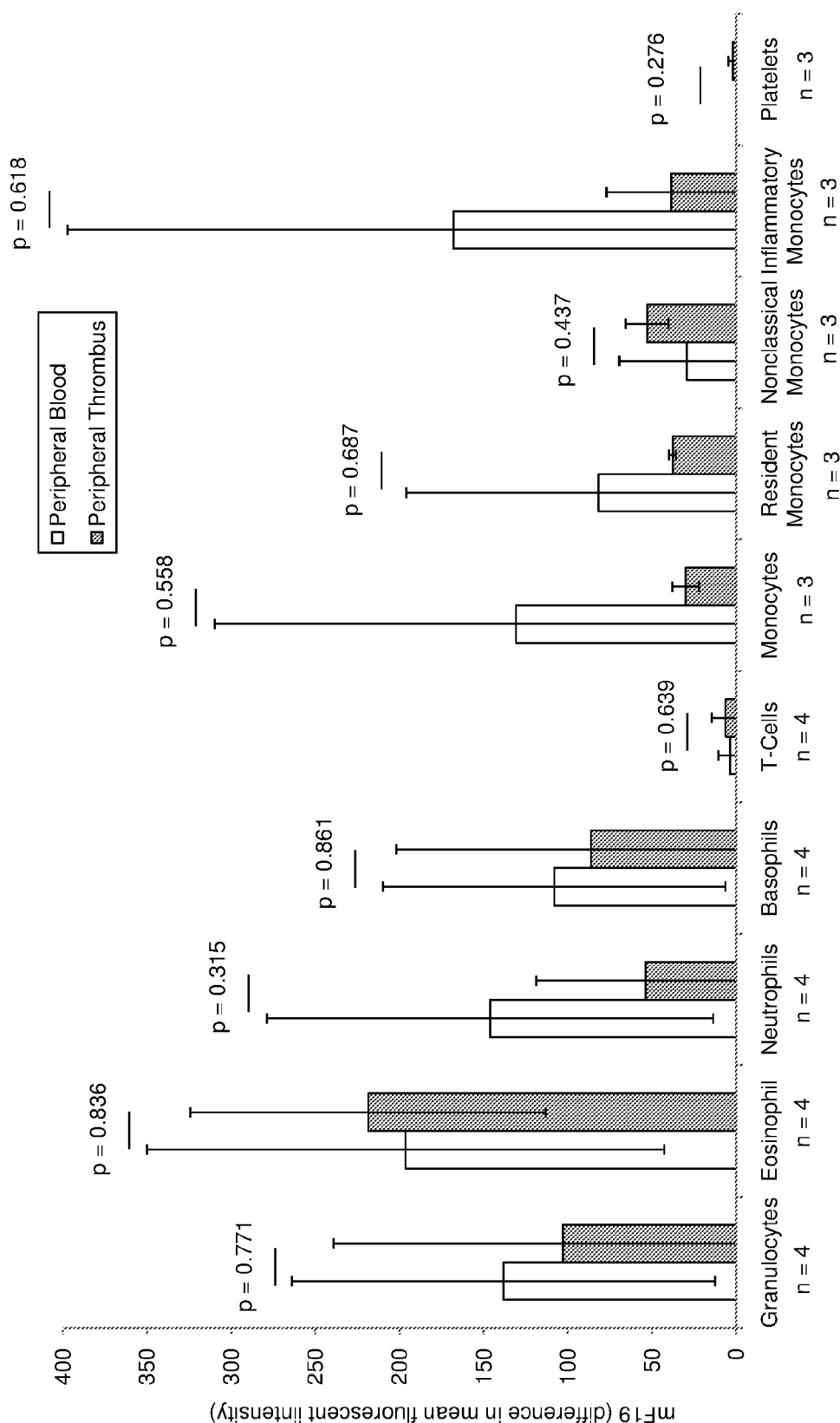
FIG. 4: Cell associated protein expression in peripheral artery thrombi vs. peripheral blood. FAP expression in peripheral blood and peripheral thrombi cell populations are calculated as the difference in mean fluorescent intensity between the signal emitted from the FAP specific antibody, and the isotype control antibody (Paired Student's T-Test). Gating for cell populations is described in FIGS. 1 and 2.

Cell Associated Protein Expression in Peripheral Artery Thrombi vs. Peripheral Blood The peripheral thrombi and blood samples are treated and the cell populations are gated as described in the methods and the Examples above. In a first step the respective numbers of the sub-cell populations in the samples are analyzed and compared to each other. Thereby it could be observed that the inflammatory monocyte subsets are decreased in their numbers whereas nonclassical and resident monocytes are increased when compared to the blood sample. In a second step and as depicted in FIG. 4, FAP expression in the respective cell populations as indicated is calculated as the difference in mean fluorescent intensity between the signal emitted from the FAP specific antibody and the isotype control antibody (Paired Student's T-Test) in peripheral blood and peripheral thrombi specimens in the same patients. As evident from FIG. 4, FAP expression is significantly unaltered in all peripheral blood vs. peripheral artery thrombus-derived cell populations.

Example 5

Cell Associated Protein Expression in Coronary Thrombi vs. Peripheral Thrombi

Figure 5:
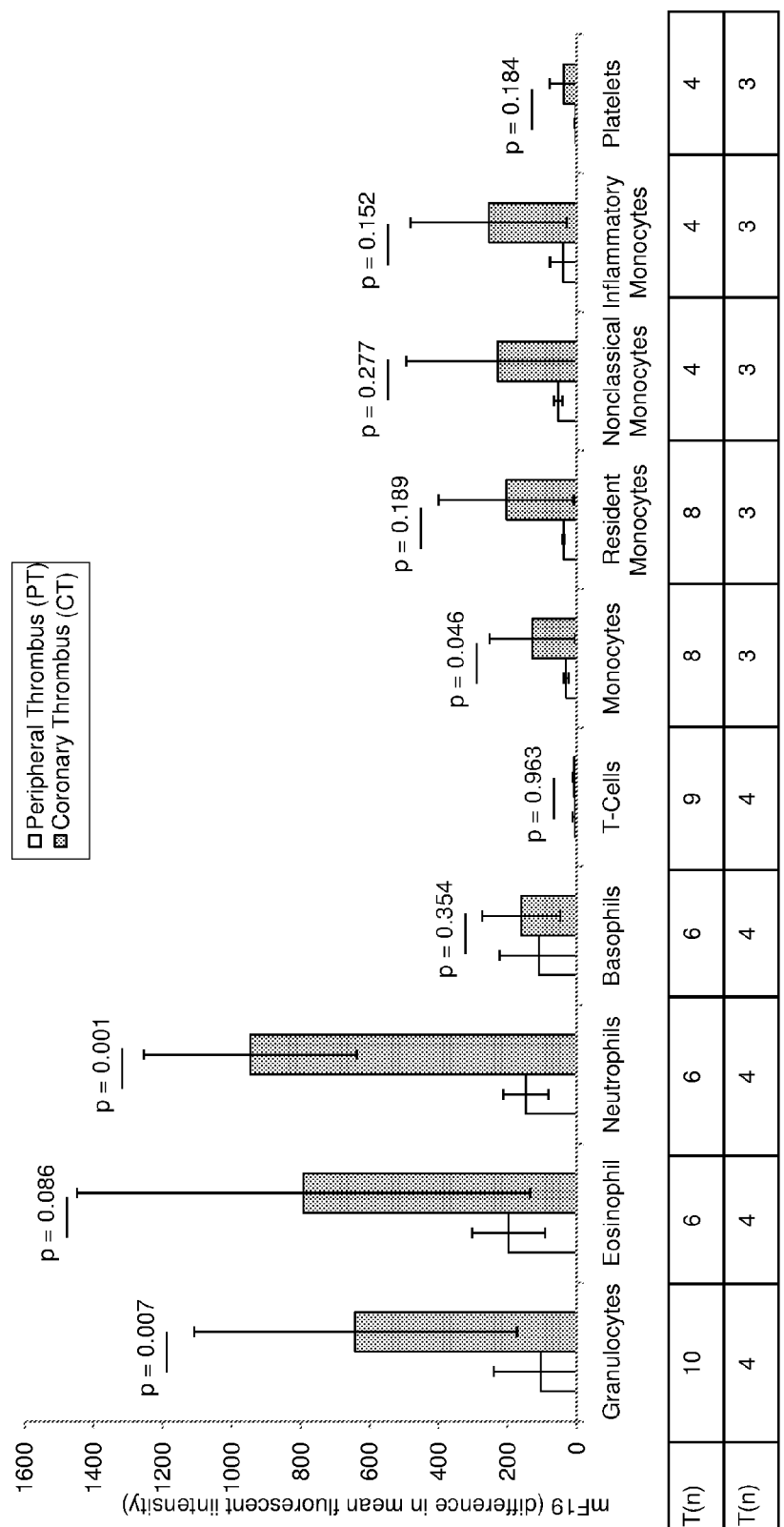
FIG. 5: Cell associated protein expression in coronary thrombi vs. peripheral thrombi. FAP expression in peripheral thrombi and coronary thrombi cell populations are calculated as the difference in mean fluorescent intensity between the signal emitted from the FAP specific antibody, and the isotype control antibody (Student's T-Test). Gating for cell populations is described in FIGS. 1 and 2.

The peripheral thrombi and coronary thrombi samples are treated and the cell populations are gated as described in the methods and the Examples above. First the leukocyte subpopulation numbers are analyzed and as a result basophils, eosinophils, and neutrophils as well as T-Cell subsets are not significantly altered in peripheral thrombi in comparison to coronary thrombi from the same patients (paired Student's T-Test). In addition, as depicted in FIG. 5, the protein associated expression of FAP in subpopulations of leukocytes is quantified as the mean fluorescent intensity generated by an FAP-specific antibody (mF19) and a matching isotype control antibody for both peripheral blood (light columns) and coronary thrombi (dark columns). Gating for cell populations is described in Examples 1-3, supra and peripheral thrombi and coronary thrombi from different patients are analyzed (C; unpaired two-tailed unequal variance student's T-test). Thus, as evident from FIG. 5, FAP expression is increased in almost all tested subpopulations. The n-values, i.e. the numbers of patient samples for coronary thrombi (CT) and peripheral blood (PT) are indicated.

Example 6

Validation of FAP Specific Binding of Anti-FAP Antibody mF19

Figure 6:
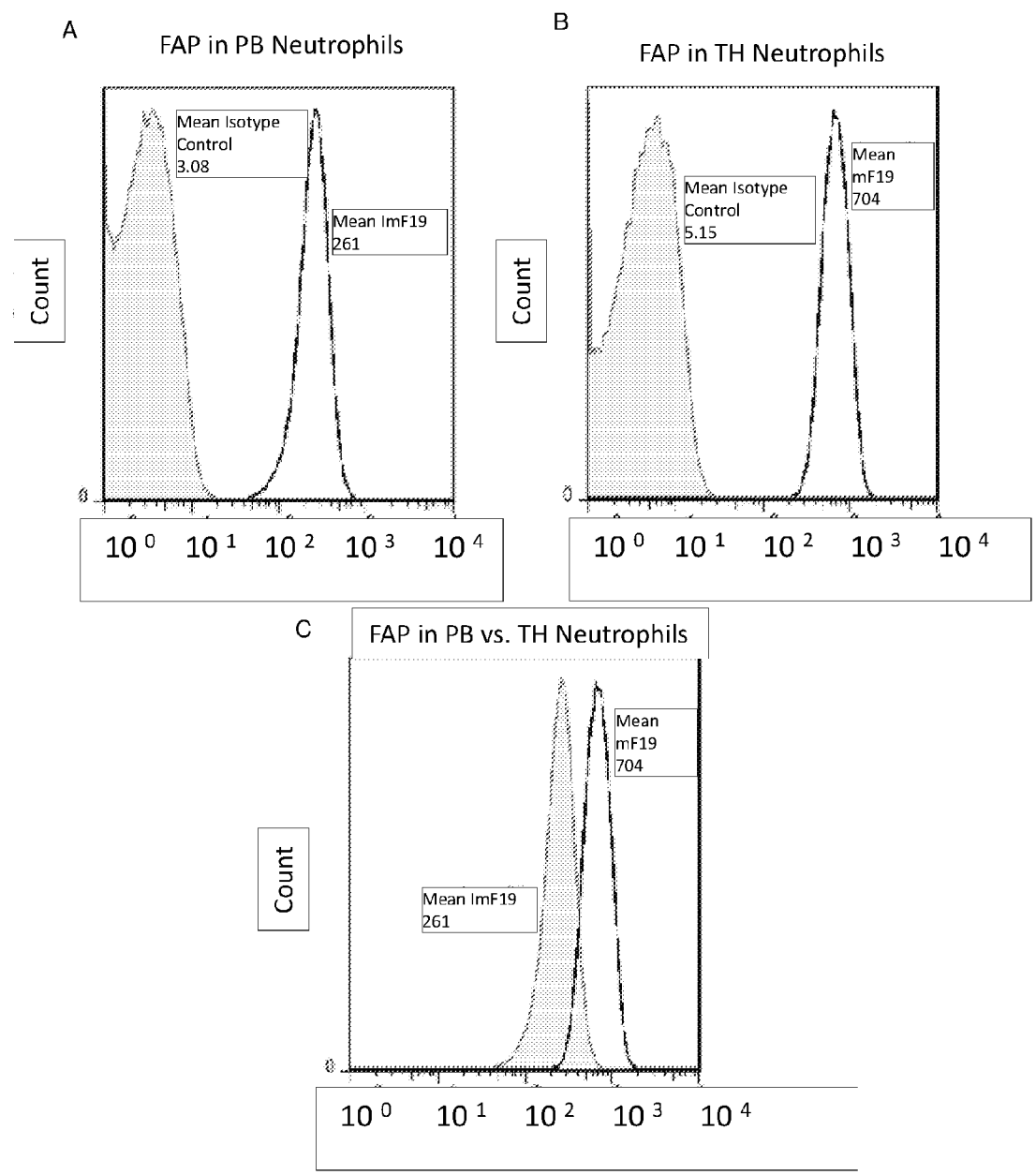
FIG. 6: Validation of FAP specific binding of anti-FAP antibody mF19. Neutrophil-associated FAP expression is enhanced in peripheral blood vs. coronary thrombi. FAP expression in neutrophils pre-gated by side scatter and CD125, is quantified as the mean fluorescent intensity from the histogram generated by an FAP-specific antibody (mF19) and a matching isotype control antibody for both peripheral blood (A) and thrombi (B). The increase of neutrophil-specific FAP expression is shown by the change of mean fluorescent intensity of the mF19 histogram for peripheral blood and thrombi (C).

Human occluding coronary thrombi are retrieved from patients who had experienced an acute myocardial infarction. One vial of peripheral blood from the same patient is taken at the same time point as a control. In order to quantify relative cell population and protein levels from the thrombi (a solid form of clotted blood) the samples are gently lysed into individual cells in preparation of a flow cytometry analysis. This one hour procedure is performed by enzymatic digestion described in the methods above. In general, the samples are processed as described in Example 2 and described in the methods, see supra. Peripheral blood from the same patient is processed in an identical manner as the thrombus, and then the cells are gated as described in Example 1 and 2 and cell populations are identified by staining the samples with the respective antibodies as indicated in Table 1. In addition, these cells are incubated with the mF19 anti-FAP antibody in order to determine and validate the binding specificity of the antibody. FAP expression in neutrophils pre-gated by side scatter and CD125 is quantified as the mean fluorescent intensity from the histogram generated by an FAP-specific antibody (mF19) and a matching isotype control antibody for both peripheral blood (PB) (6A) and thrombi (TH) (6B). The increase of neutrophil-specific FAP expression is shown by the change of mean fluorescent intensity of the mF19 histogram for peripheral blood and thrombi (6 C). The mean numbers indicates the intensity values (from the x-axisis). As evident from the histogram depicted in FIG. 6 C a shift in the fluorescence signal from the neutrophils of the blood sample towards higher intensity of the thrombi sample cells can be observed. Thus, mF19 specifically binds to neutrophils of the thrombus sample.

The invention claimed is:

1. A method for determining or validating the therapeutic or diagnostic utility of an antibody in coronary atherothrombosis comprising
(a) subjecting a candidate antibody labeled with a fluorescent tag to a sample of a thrombus obtained from a patient who had experienced an acute cardiovascular condition and determining the binding of the antibody to
(i) at least one specific cell population, wherein the at least one specific cell population is one or more of T cells, monocytes, eosinophils, neutrophils or granulocytes; and/or (ii) a cell-specific protein, wherein the protein is specific for the disease, and
wherein the expression of the protein is associated with the at least one specific cell population, and
(b) calculating the difference mean fluorescent intensity between the level of specific-binding for the candidate antibody and a non-specific isotype control antibody compared to the level of specific and non-specific binding in a control sample by
(iii) calculating the mean fluorescent intensity of the candidate antibody by subtracting the signal given by a non-specific isotype control antibody in thrombi from the signal given by the candidate antibody in thrombi;
(iv) subtracting the fluorescent intensity of the control antibody for peripheral blood or peripheral thrombus from the signal given by the candidate antibody in a control sample of peripheral blood or peripheral thrombus; and
(v) subtracting the mean fluorescent intensity calculated in (iv) from the mean fluorescent intensity calculated in (iii),
wherein the difference mean fluorescent intensity is indicative for the utility of the candidate antibody as a therapeutic or diagnostic means, wherein the binding is determined by fluorescence activated cytometry.

2. The method of claim 1, wherein an increased level of binding of the antibody indicates its utility as a drug.

3. The method of claim 1 or 2, wherein the antibody is selected from the group consisting of single Fc fragment (scFv), an F(ab') fragment, an F(ab) fragment and an F(ab')$_2$ fragment.

4. The method of claim 1, wherein an altered level of binding of the antibody to the cell population and/or the protein compared to the level of binding in a control sample indicates the utility of the antibody as a therapeutic or diagnostic means.

5. The method of claim 1, wherein the coronary atherothrombosis is selected from a group consisting of myocardial infarction, stroke, venous thrombosis, deep vein thrombosis, portal vein thrombosis, renal vein thrombosis, jugular vein thrombosis, Budd-Chiari syndrome, Paget-Schroetter disease, cerebral venous sinus thrombosis, coronary stent occlusion, pulmonary embolism and coronary bypass graft occlusion.

6. The method of claim 1, wherein the control sample is selected from peripheral blood or a peripheral arterial thrombus.

7. The method of claim 1, wherein the thrombus is selected from the group consisting of traditional atherothrombotic coronary thrombus, coronary stent thrombus, coronary bypass thrombus, pulmonary embolus and venous thrombus.

8. The method of claim 1, wherein an altered cell number is observed in at least one cell population selected from the group consisting of CD14 dim-hi monocytes, granulocytes, eosinophils, neutrophils, cytotoxic T-cells, double negative T-cells, helper T-cells and CD28 helper T-cells.

9. The method of claim 4, wherein
(i) the altered level of the cell population relates to the number and/or status of the cells of said cell population; and/or wherein
(ii) an altered cell number is observed in at least one cell population selected from the group consisting of monocytes, eosinophils, neutrophils and/or granulocytes.

10. The method of claim 9, wherein an altered cell number is observed in at least one cell population selected from the group consisting of CD14 dim-hi monocytes, granulocytes, eosinophils, neutrophils, cytotoxic T-cells, double negative T-cells, helper T-cells, and/or CD28-Helper T-cells.

* * * * *